United States Patent

Estanove et al.

[11] Patent Number: 6,057,461
[45] Date of Patent: May 2, 2000

[54] METHOD FOR PREPARING SUBSTITUTED ANTHRAQUINONE AND APPLICATION TO THE PREPARATION OF RHEINS

[75] Inventors: Cyril Estanove, Boulogne; François Pruvost, Quimper, both of France

[73] Assignee: Girex, Quimper, France

[21] Appl. No.: 09/155,643

[22] PCT Filed: Feb. 2, 1998

[86] PCT No.: PCT/FR98/00189

§ 371 Date: Oct. 2, 1998

§ 102(e) Date: Oct. 2, 1998

[87] PCT Pub. No.: WO98/33757

PCT Pub. Date: Aug. 6, 1998

[30] Foreign Application Priority Data

Feb. 3, 1997 [FR] France ................... 97 01161

[51] Int. Cl.[7] .............. C07C 49/593; C07C 50/18; C07C 46/00
[52] U.S. Cl. .............. 552/262; 552/265; 552/266; 552/268
[58] Field of Search .................. 552/262, 265, 552/266, 268

[56] References Cited

U.S. PATENT DOCUMENTS 5,723,675  3/1998  Joo et al. ................... 568/317

FOREIGN PATENT DOCUMENTS 2 190 080  11/1987  United Kingdom .
97/16404   5/1997   WIPO .

OTHER PUBLICATIONS

M.E. Jung et al., J.C.S. Chem. Comm., pp. 95–96, 1978.
Petrzilka and J.I. Grayson, Synthesis, pp. 753–760, 1981.
G. Jesaitis et a., J. Chem Ed., 49, pp. 436–437, 1972.
T. Watamatsu et al., Synthetic Communications, 14, pp. 1167–1173, 1984.
Krohn, Leibigs Ann. Chem., 1981, pp. 2285–2297 (Abstract Only).
Krohn et al., Tetrahedron, vol. 40, No. 19, pp. 3677–3694.
Thomas et al., J. Org. Chem. vol. 53, No. 18, pp. 4201–4209.
Database WPI XP 002008450.
Boisvert et al., Regiospecific Addition of Monooxygenated Dienes to Halo Quinones, J. Org. Chem., 53, 4052–59, 1988.

Kraus et al., A Formal Total Synthesis of Aklavinone Tetrahedron Letters, 27, 1873–76, 1986.
Laugraud et al., Regioselective Synthesis of 2– and 3–(Phenylthio)juglone Derivatives, 1557–60, 1988.

*Primary Examiner*—Jose' G. Dees
*Assistant Examiner*—Alton Pryor
*Attorney, Agent, or Firm*—Burns, Doane, Swecker & Mathis, L.L.P.

[57] ABSTRACT

The invention relates to a process for the preparation of substituted anthraquinones represented by the general formula (I):

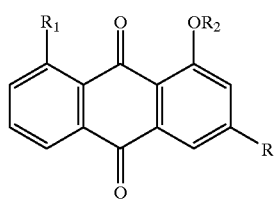

(I)

by Diels-Alder reaction between a 1,4-naphthoquinone of general formula (II):

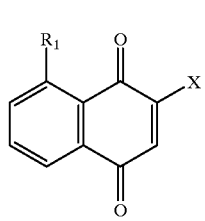

(II)

and an acyclic diene of formula (III):

$$CH_2=CR-CH=CH-OR_3 \qquad (III)$$

followed by an oxidizing deprotection reaction by means of the Jones reagent, in order to obtain the substituted anthraquinone of general formula (I).

Application to the preparation of rheins of use in pharmaceuticals.

20 Claims, No Drawings

METHOD FOR PREPARING SUBSTITUTED ANTHRAQUINONE AND APPLICATION TO THE PREPARATION OF RHEINS

This application is a 371 of PCT/FR 98/00189 filed Feb. 2, 1998.

The present invention relates to a novel process for the preparation of substituted anthraquinones from 1,4-naphthoquinones and to the application of the products obtained as intermediates in the synthesis of products exhibiting therapeutically useful properties.

The preparation of anthraquinones, such as chrysophanol, by addition of 6-methoxy-4-methylpyrone to a naphthoquinone such as juglone, according to the Diels-Alder reaction, has been described by M. E. Jung et al., *J.C.S. Chem. Comm.*, 95 (1978). However, this process requires several stages, that is to say an addition, followed by an oxidation with silver oxide, to cause aromatization of the rings, and a demethylation. Furthermore, the reaction involves the use of diazomethane, which has well known disadvantages.

Patent GB-A-2,190,080 discloses a process for the preparation of anthraquinones by the reaction of a butadiene derivative with a naphthoquinone in the presence of a catalyst based on a transition metal but this process has to be carried out in a chamber kept under high pressure.

The routes for the synthesis of anthracyclinones by a Diels-Alder cycloaddition reaction have also been described by M. Petrzilka and J. I. Grayson [*Synthesis*, 753 (1981)]. According to these authors, the regiospecific addition reaction of a diene to a quinone can be produced by using, as catalyst, a Lewis acid consisting of the compound $BF_3 \cdot O(C_2H_5)_2$.

The process according to the present invention makes it possible to prepare substituted anthraquinones represented by the general formula (I) hereinbelow:

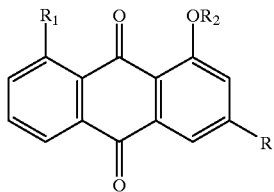

(I)

from 1,4-naphthoquinones in only two stages and with an excellent yield.

In the general formula (I) hereinabove, R represents a hydrogen atom or a linear or branched alkyl group comprising 1 to 5 carbon atoms, a chloromethyl group, a —COCl group, a —COOR' group or a —CH$_2$OR' group where R' is a hydrogen atom or a linear or branched alkyl group comprising 1 to 5 carbon atoms, $R_1$ represents a hydrogen atom, a hydroxyl group, a linear or branched alkoxy group comprising 1 to 5 carbon atoms or an acyloxy group comprising 1 to 5 carbon atoms and $R_2$ represents a hydrogen atom. If appropriate, an acetylation can be carried out in order to obtain the compound of formula (I) where $R_2$ is an acetyl group.

In accordance with the process according to the invention, in a first step, a Diels-Alder reaction is carried out between a 1,4-naphthoquinone of general formula (II):

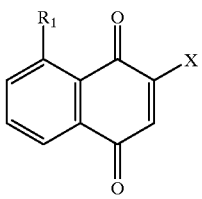

(II)

in which $R_1$ represents a hydrogen atom, a hydroxyl group, a linear or branched alkoxy group comprising 1 to 5 carbon atoms or an acyloxy group comprising 1 to 5 carbon atoms and X represents a hydrogen or halogen atom, and an acyclic diene of general formula (III):

$$CH_2{=}CR{-}CH{=}CH{-}OR_3 \qquad (III)$$

in which R represents a hydrogen atom or a linear or branched alkyl group comprising 1 to 5 carbon atoms, a chloromethyl group, a —COCl group, a —COOR' group or a —CH$_2$OR' group where R' is a hydrogen atom or a linear or branched alkyl group comprising 1 to 5 carbon atoms and $R_3$ represents a silyl group of formula —Si(R$_4$)$_3$ where $R_4$ is a linear or branched alkyl group comprising 1 to 5 carbon atoms, in order to obtain a substituted 1, 1a, 4, 4a-tetrahydroanthraquinone [sic] of general formula (IV):

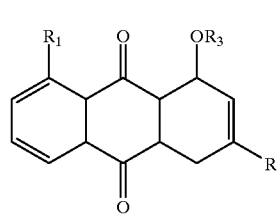

(IV)

in which R, $R_1$ and $R_3$ have the definitions indicated hereinabove, and then an oxidizing deprotection reaction is carried out, by means of the Jones reagent, on the tetrahydroanthraquinone of general formula (IV), in order to obtain the desired anthraquinone, represented by the general formula (I) shown hereinabove.

The oxidizing deprotection reaction is preferably carried out by reaction with a mixture of potassium dichromate and aqueous sulfuric acid in a solvent, such as acetic acid, ethyl ether, dimethyl sulfoxide or dichloromethane, in the presence of a phase transfer agent, such as a quaternary ammonium salt, or alternatively a ketone and preferably acetone.

In the above formula (II) representing the starting naphthoquinone, $R_1$ preferably represents a hydroxyl or acetoxy group and X is preferably a hydrogen atom or a chlorine atom. In the general formula (III) representing the acyclic diene, it is preferable for $R_3$ to represent a trimethylsilyl group and R a hydrogen atom or a methyl group.

The acyclic diene used in the reaction described hereinabove can be a butadiene derivative, such as, for example, 1-(trimethylsilyloxy)-1,3-butadiene and 3-methyl-1-(trimethylsilyloxy)-1,3-butadiene.

Use is preferably made, among the naphthoquinones of general formula (II), of juglone, represented by the formula (II) where $R_1$ represents a hydroxyl group, or 3-chlorojuglone, represented by the same formula where X is a chlorine atom. Juglone can be prepared, for example, by oxidation of 1,5-dihydroxynaphthalene in the presence of an appropriate catalyst as described in Patent SU-1,817,767 or by chromium oxide by the method of G. Jesaitis et al., *J. Chem. Ed.*, 49, 436 (1972) or by oxidation by means of oxygen in the presence of a cobalt-based catalyst, such as salcomine, according to the method of T. Wakamatsu et al., *Synthetic Communications*, 14, 1167 (1984).

The Diels-Alder cycloaddition reaction between the 1,4-naphthoquinone of general formula (II) and the acyclic diene of general formula (III) is preferably carried out in a solvent which can be chosen from hydrocarbon-comprising solvents and alcohols, such as toluene, benzene or methanol. According to an advantageous embodiment of the invention, the reaction is carried out in the presence of a catalytic amount of hydroquinone. It can also be advantageous to carry out the reaction in the presence of a Lewis catalyst chosen, for example, from zinc chloride, ferric chloride and boron triacetate.

The addition reaction is preferably carried out at room temperature or while gently heating at a temperature between 20 and 50° C.

As indicated hereinabove, an oxidizing deprotection reaction is carried out on the tetrahydroanthraquinone of general formula (IV) by means of the Jones reagent, which makes it possible, entirely simultaneously, to bring about the desilylation, the oxidation and the aromatization in a single step, in order to obtain the desired anthraquinone represented by the general formula (I) with a good yield. This reaction can advantageously be carried out while cold and preferably at a temperature of approximately 0° C. in an appropriate solvent in a single stage, without it being necessary to isolate an intermediate product, in contrast to the known processes. For example, according to the known techniques (see K. Krohn, Liebigs Ann. Chem. (1981), p. 2285–2297), chrysophanol can be prepared in three stages from a napthoquinone [sic], on which is carried out a Diels-Alder reaction, in order to obtain a tetrahydroanthraquinone, which subsequently has to be treated by hydrolysis in order to bring about the desilylation, and then a treatment with a chromium-based oxidizing agent, such as pyridinium chlorochromate, is carried out in order to be able to obtain the desired product, in the form of a mixture of chrysophanol and isochrysophanol.

The process conforms [sic] with the present invention is particularly advantageous in that it makes it possible easily to obtain the desired anthraquinone, that is to say a compound comprising aromatic rings, without the use of compounds, such as silver oxide, for bringing about aromatization, in contrast to conventional reaction schemes. Furthermore, the process of the present invention makes it possible to obtain isomer-free substituted anthraquinones, for example chrysophanol, with a good yield, while reducing the amounts of chromium derivatives used.

The substituted anthraquinones obtained by the process according to the present invention can be used in the preparation of rheins of general formula (V)

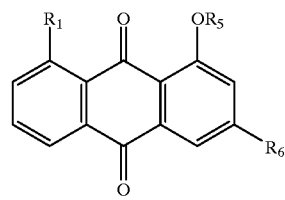

in which $R_5$ represents an acetyl group and $R_6$ represents a —$CO_2R'$ group where R' is a hydrogen atom or a linear or branched alkyl group comprising 1 to 5 carbon atoms, which are obtained by carrying out an acetylation of the substituted anthraquinones of general formula (I), followed, if necessary, by an oxidation and a purification.

These rheins are of use in human and veterinary therapeutics as active principles or medicaments, in particular as non-steroidal anti-inflammatories in the treatment of arthritis and arthrosis.

The following examples illustrate the invention in more detail without limiting the scope thereof.

EXAMPLE 1

A mixture of 0.4 g of 5-hydroxy-1,4-naphthoquinone ($2.3 \times 10^{-3}$ mol) and of 0.47 g of 3-methyl-1-(trimethylsilyloxy)-1,3-butadiene ($3.0 \times 10^{-3}$ mol) in 5 ml of dichloromethane or of toluene is reacted at room temperature and under a nitrogen atmosphere in a 25 ml round-bottomed flask in the presence of a catalytic amount of hydroquinone. Stirring is maintained for approximately 14 hours.

The change in the reaction is monitored by thin layer chromatography. The reaction is completed when the juglone is no longer detected.

The solvent is removed by distillation under reduced pressure. After precipitating with a minimum amount of pentane, the solid is filtered off and 728 mg of a mixture consisting of 90% of 8-hydroxy-3-methyl-1-(trimethylsilyloxy)-1,1a,4,4a-tetrahydro-9,10-anthraquinone [sic] ($1.98 \times 10^{-3}$ mol) and of 10% of 5-hydroxy-3-methyl-1-(trimethylsilyloxy)-1,1a,4,4a-tetrahydro-9,10-anthraquinone [sic] ($0.22 \times 10^{-3}$ mol) are obtained.

The Diels-Alder adducts are subsequently stirred in the presence of 8.5 ml of Jones reagent (1.67 g of potassium dichromate ($5.68 \times 10^{-3}$ mol)+7 ml of water+1.3 ml of concentrated sulfuric acid) in 70 ml of acetone. The reaction is complete after 15 minutes at 0° C. The excess oxidizing agent is destroyed with isopropanol before filtering the chromium salts on celite. The acetone is evaporated in order to allow the chrysophanol and the isochrysophanol to precipitate. After filtering, 527 mg of a mixture consisting of 90% of chrysophanol ($1.87 \times 10^{-3}$ mol) and of 10% of isochrysophanol ($0.2 \times 10^{-3}$ mol) are obtained, which is equivalent to an overall yield of 90%.

EXAMPLE 2

The preparation is carried out as in Example 1 but, after the Diels-Alder reaction, the solvent is removed by distillation under reduced pressure and crystallization from petroleum ether makes it possible to obtain 531 mg of 8-hydroxy-3-methyl-1-(trimethylsilyloxy)-1,1a,4,4a-tetrahydro-9,10-anthraquinone [sic] ($1.6 \times 10^{-3}$ mol) without the presence of the other isomer.

The Diels-Alder adduct is subsequently treated with 6.2 ml of Jones reagent, in order to obtain, after treatment, 384 mg of chrysophanol ($1.51 \times 10^{-3}$ mol), which is equivalent to an overall yield of chrysophanol of 66%.

EXAMPLE 3

The preparation is carried out as in Example 1 but adding 0.1 equivalent of $B(OAc)_3$ as catalyst, as Lewis acid, during the Diels-Alder reaction.

The reaction takes place in the same way and the juglone is no longer detected by thin layer chromatography after stirring overnight.

The solvent is removed by distillation under reduced pressure. After precipitating with a minimum amount of pentane, the solid is filtered off and 728 mg of a mixture consisting of 95% of 8-hydroxy-3-methyl-1-(trimethylsilyloxy)-1,1a,4,4a-tetrahydro-9,10-anthraquinone [sic] ($2.09 \times 10^{-3}$ mol) and of 5% of 5-hydroxy-3-methyl-1-(trimethylsilyloxy)-1,1a,4,4a-tetrahydro-9,10-anthraquinone [sic] ($0.11 \times 10^{-3}$ mol) are obtained.

The Diels-Alder adducts are subsequently treated with 8.5 ml of Jones reagent in order to obtain, after treatment, 527 mg of a mixture consisting of 95% of chrysophanol ($1.97 \times 10^{-3}$ mol) and of 5% of isochrysophanol ($0.10 \times 10^{-3}$ mol), which is equivalent to an overall yield of 90%.

EXAMPLE 4

The preparation is carried out as in Example 1 but using only 2.8 ml of Jones reagent.

After treatment, 460 mg of a mixture consisting of 90% of chrysophanol ($1.63 \times 10^{-3}$ mol) and of 10% of isochrysophanol ($0.18 \times 10^{-3}$ mol) are obtained, which is equivalent to an overall yield of 79%.

EXAMPLE 5

The preparation is carried out as in Example 2 but using only 2.8 ml of Jones reagent.

After treatment, 335 mg of chrysophanol ($1.32 \times 10^{-3}$ mol) are obtained, which is equivalent to an overall yield of chrysophanol of 57%.

EXAMPLE 6

The preparation is carried out as in Example 1 but reacting 0.36 g of 1,4-naphthoquinone ($2.3 \times 10^{-3}$ mol) and 0.47 g of 3-methyl-1-(trimethylsilyloxy)-1,3-butadiene ($3.0 \times 10^{-3}$ mol).

After reaction with the Jones reagent and treatment, 494 mg of 1-hydroxy-3-methyl-9,10-anthraquinone ($2.07 \times 10^{-3}$ mol) are obtained, which is equivalent to an overall yield of 90%.

EXAMPLE 7

The preparation is carried out as in Example 1 reacting 0.36 g of 1,4-naphthoquinone ($2.3 \times 10^{-3}$ mol) and 0.47 g of 3-methyl-1-(trimethylsilyloxy)-1,3-butadiene ($3.0 \times 10^{-3}$ mol) and using only 2.8 ml of Jones reagent.

After reaction with the Jones reagent and treatment, 431 mg of 1-hydroxy-3-methyl-9,10-anthraquinone ($1.81 \times 10^{-3}$ mol) are obtained, which is equivalent to an overall yield of 79%.

EXAMPLE 8

The preparation is carried out as in Example 1 but reacting 0.4 g of 5-hydroxy-1,4-naphthoquinone ($2.3 \times 10^{-3}$ mol) and 0.42 g of 1-(trimethylsilyloxy)-1,3-butadiene ($3.0 \times 10^{-3}$ mol).

After reaction with the Jones reagent and treatment, 498 mg of a mixture consisting of 90% of 1,8-dihydroxy-9,10-anthraquinone ($1.87 \times 10^{-3}$ mol) and of 10% of 1,5-dihydroxy-9,10-anthraquinone ($0.2 \times 10^{-3}$ mol) have [sic] obtained, which is equivalent to an overall yield of 90%.

EXAMPLE 9

The preparation is carried out as in Example 1 but adding 63 mg of zinc chloride as catalyst, as Lewis acid, in the first stage.

The reaction takes place in the same way and the juglone is no longer detected by thin layer chromatography after 14 hours.

520 mg of a mixture consisting of 60% of 8-hydroxy-3-methyl-1-(trimethylsilyloxy)-1,1a,4,4a-tetrahydroanthraquinone [sic] and of 40% of 8-hydroxy-2-methyl-4-trimethylsilyloxy-1,1a,4,4a-tetrahydro-anthraquinone [sic] are thus obtained.

These two isomers are treated in acetone with stirring with the same Jones reagent as in Example 1. After removing excess oxidizing agent, filtering off the chromium salts and evaporating the solvent, a mixture of 60% of chrysophanol and 40% of isochrysophanol is obtained with an overall yield of 64%.

EXAMPLE 10 (COMPARATIVE EXAMPLE)

A mixture of 0.87 g of 5-hydroxy-1,4-naphthoquinone and of 0.94 g of 3-methyl-1-(trimethylsilyloxy)-1,3-butadiene in 3 ml of dichloromethane is reacted at room temperature in a 5 ml round-bottomed flask for approximately 12 hours.

The change in the reaction is monitored by thin layer chromatography. The reaction is completed when the juglone is no longer detected.

A mixture consisting of 90% of 8-hydroxy-3-methyl-1-(trimethylsilyloxy)-1,1a,4,4a-tetrahydro-anthraquinone [sic] and of 10% of 8-hydroxy-2-methyl-4-(trimethylsilyloxy)-1,1a,4,4a-tetrahydroanthraquinone [sic] is thus obtained.

The two isomers as a mixture are desilylated in acidic medium (1N HCl, 0.5 ml in 5 ml of methanol) and then oxidized and aromatized using pyridinium chlorochromate (2.36 g) in 100 ml of dichloromethane, the mixture being kept stirring for approximately 4 hours. After addition of 2 g of magnesium sulfate and filtration, followed by evaporation of the solvent under reduced pressure, a mixture of chrysophanol and of isochrysophanol is obtained.

The chrysophanol/isochrysophanol mixture thus obtained with a yield of 50% is identified by NMR.

This example shows that the yield is markedly lower when the preparation is carried out in three stages according to the conventional technique, without use of the Jones reagent.

We claim:

1. Process for the preparation of substituted anthraquinones represented by the general formula (I) hereinbelow

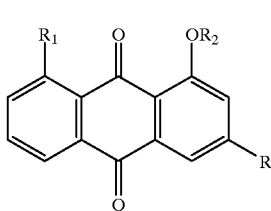

(I)

in which R represents a hydrogen atom or a linear or branched alkyl group comprising 1 to 5 carbon atoms, a chloromethyl group, a —COCl group, a —COOR' group or a —CH₂OR' group where R' is a hydrogen atom or a linear or branched alkyl group comprising 1 to 5 carbon atoms, $R_1$ represents a hydrogen atom, a hydroxyl group, a linear or branched alkoxy group comprising 1 to 5 carbon atoms or an acyloxy group comprising 1 to 5 carbon atoms and $R_2$ represents a hydrogen atom, characterized in that a Diels-Alder reaction is carried out between a 1,4-naphthoquinone of general formula (II):

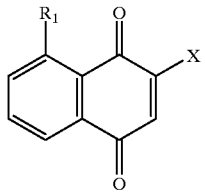

(II)

in which $R_1$ represents a hydrogen atom, a hydroxyl group, a linear or branched alkoxy group comprising 1 to 5 carbon atoms or an acyloxy group comprising 1 to 5 carbon atoms and X represents a hydrogen or halogen atom, and an acyclic diene of formula (III):

(III)

in which R represents a hydrogen atom or a linear or branched alkyl group comprising 1 to 5 carbon atoms, a chloromethyl group, a —COCl group, a —COOR' group or a —CH₂OR' group where R' is a hydrogen atom or a linear or branched alkyl group comprising 1 to 5 carbon atoms and $R_3$ represents a silyl group of formula —Si(R₄)₃ where $R_4$ is a linear or branched alkyl group comprising 1 to 5 carbon atoms, in order to obtain a substituted tetrahydroanthraquinone of general formula (IV):

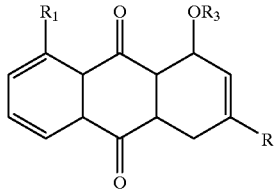

(IV)

in which R, $R_1$ and $R_3$ have the definitions indicated hereinabove, and then an oxidizing deprotection reaction is carried out, by means of the Jones reagent, on the tetrahydroanthraquinone of general formula (IV), in order to obtain the anthraquinone of general formula (I).

2. Process according to claim 1, characterized in that the reaction is carried out in the presence of a Lewis acid.

3. Process according to claim 2, characterized in that the Lewis acid is chosen from zinc chloride, ferric chloride and boron triacetate.

4. Process according to claim 1, characterized in that the reaction is carried out in the presence of a catalytic amount of hydroquinone.

5. Process according to claim 1, characterized in that $R_1$ represents a hydroxyl or acetoxy group and X is a hydrogen atom or a chlorine atom.

6. Process according to claim 1, characterized in that R represents a hydrogen atom or a methyl group and $R_3$ represents a trimethylsilyl group.

7. Process according to claim 6, characterized in that the diene of formula (III) is 1-(trimethylsilyloxy)-1,3-butadiene or 3-methyl-1-(trimethylsilyloxy)-1,3-butadiene.

8. Process according to claim 5, characterized in that the naphthoquinone of general formula (II) is juglone or 3-chlorojuglone.

9. Process according to claim 1, characterized in that the oxidizing deprotection reaction of the tetrahydroanthraquinone of formula (IV) is carried out by means of a mixture based on potassium dichromate and on sulfuric acid.

10. Process according to claim 9, characterized in that the oxidizing deprotection reaction is carried out in a solvent chosen from acetic acid, ethyl ether, dimethyl sulfoxide, dichloromethane or a ketone.

11. Process according to claim 2, characterized in that $R_1$ represents a hydroxyl or acetoxy group and X is a hydrogen atom or a chlorine atom.

12. Process according to claim 4, characterized in that $R_1$ represents a hydroxyl or acetoxy group and X is a hydrogen atom or a chlorine atom.

13. Process according to claim 2, characterized in that R represents a hydrogen atom or a methyl group and $R_3$ represents a trimethylsilyl group.

14. Process according to claim 4, characterized in that R represents a hydrogen atom or a methyl group and $R_3$ represents a trimethylsilyl group.

15. Process according to claim 5, characterized in that R represents a hydrogen atom or a methyl group and $R_3$ represents a trimethylsilyl group.

16. Process according to claim 2, characterized in that the oxidizing deprotection reaction of the tetrahydroanthraquinone of formula (IV) is carried out by means of a mixture based on potassium dichromate and on sulfuric acid.

17. Process according to claim 4, characterized in that the oxidizing deprotection reaction of the tetrahydroanthraquinone of formula (IV) is carried out by means of a mixture based on potassium dichromate and on sulfuric acid.

18. Process according to claim 15, characterized in that the oxidizing deprotection reaction of the tetrahydroanthraquinone of formula (IV) is carried out by means of a mixture based on potassium dichromate and on sulfuric acid.

19. A process for preparing rheins of general formula (V)

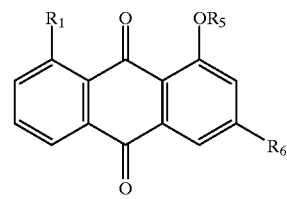

(V)

in which $R_5$ represents an acetyl group, $R_6$ represents a —CO₂R' group where R' is a hydrogen atom or a linear or branched alkyl group comprising 1 to 5 carbon atoms, the process comprising aceytlating the substituted anthraquinones of general formula (I) prepared by the process of claim 1.

20. The process of claim 19, wherein the aceytlation of the substituted anthraquinones is followed by an oxidation step.

* * * * *